United States Patent

Chang et al.

[11] Patent Number: 5,238,681
[45] Date of Patent: Aug. 24, 1993

[54] INSECT BAIT STATION

[75] Inventors: Frank N. Chang, Dresher; Michael J. Gehret, Lebanon, both of Pa.

[73] Assignee: Temple University - Of the Commonwealth System of Higher Education, Philadelphia, Pa.

[21] Appl. No.: 837,531

[22] Filed: Feb. 14, 1992

Related U.S. Application Data

[63] Continuation of Ser. No. 523,011, May 14, 1990, abandoned.

[51] Int. Cl.⁵ .......................................... A01N 63/00
[52] U.S. Cl. ...................................... 424/405; 43/114; 43/131; 43/132.1; 424/78.31; 424/84; 424/93 R; 424/484; 424/485; 424/486; 424/488; 426/1; 526/238.22; 526/930
[58] Field of Search ............ 424/405, 84, 78, 93, 424/81, 484, 485, 486, 488, 78.31, 93 R; 43/114, 131, 132.1; 426/1; 526/238.22, 930

[56] References Cited

U.S. PATENT DOCUMENTS

| | | | |
|---|---|---|---|
| 170,505 | 11/1875 | Barthel | 43/131 |
| 2,157,953 | 6/1938 | De Long | 43/131 |
| 3,152,040 | 10/1964 | Fondren | |
| 3,224,145 | 12/1965 | Ballard | 43/131 X |
| 3,303,599 | 2/1967 | Ballard | 43/131 X |
| 3,337,395 | 8/1967 | Page | 424/405 X |
| 3,975,350 | 8/1976 | Hudgin et al. | 524/108 |
| 4,110,431 | 8/1978 | Oita | 424/78.26 |
| 4,178,366 | 12/1979 | Bedding | 424/93 R |
| 4,237,113 | 12/1980 | Cardarelli | 514/86 |
| 4,326,052 | 4/1982 | Kang et al. | 536/123 |
| 4,326,053 | 4/1982 | Kang et al. | 536/123 |
| 4,503,084 | 3/1985 | Baird et al. | 426/573 |
| 4,563,836 | 11/1986 | Woodruff | 43/131 |
| 4,581,845 | 4/1986 | Burkholder et al. | 43/107 |
| 4,584,337 | 4/1986 | Lee et al. | 524/500 |
| 4,615,883 | 10/1986 | Nelsen et al. | 424/408 X |
| 4,753,799 | 6/1988 | Nelsen et al. | 424/408 |
| 4,783,510 | 11/1988 | Saotome | 525/329.7 |
| 4,823,506 | 4/1989 | Demarest et al. | 43/131 |
| 4,841,669 | 6/1989 | Demarest et al. | 43/131 |
| 4,859,377 | 8/1989 | Shasha et al. | 424/488 X |
| 4,874,611 | 10/1989 | Wilson et al. | 424/410 |
| 4,889,918 | 12/1989 | Krieg et al. | 424/405 X |
| 4,921,703 | 5/1990 | Higuchi et al. | 424/419 |
| 5,057,315 | 10/1991 | Gunner et al. | 424/93 Q |
| 5,057,316 | 10/1991 | Gunner et al. | 424/93 Q |

Primary Examiner—Thurman K. Page
Assistant Examiner—Robert H. Harrison
Attorney, Agent, or Firm—Ratner & Prestia

[57] ABSTRACT

An insect bait station comprising a first compartment with a hydrated macrogel containing at least one species of entomopathogen and a second compartment containing a hydrated water retentive compound layer which acts as a water-reservoir for the entomopathogen.

22 Claims, 1 Drawing Sheet

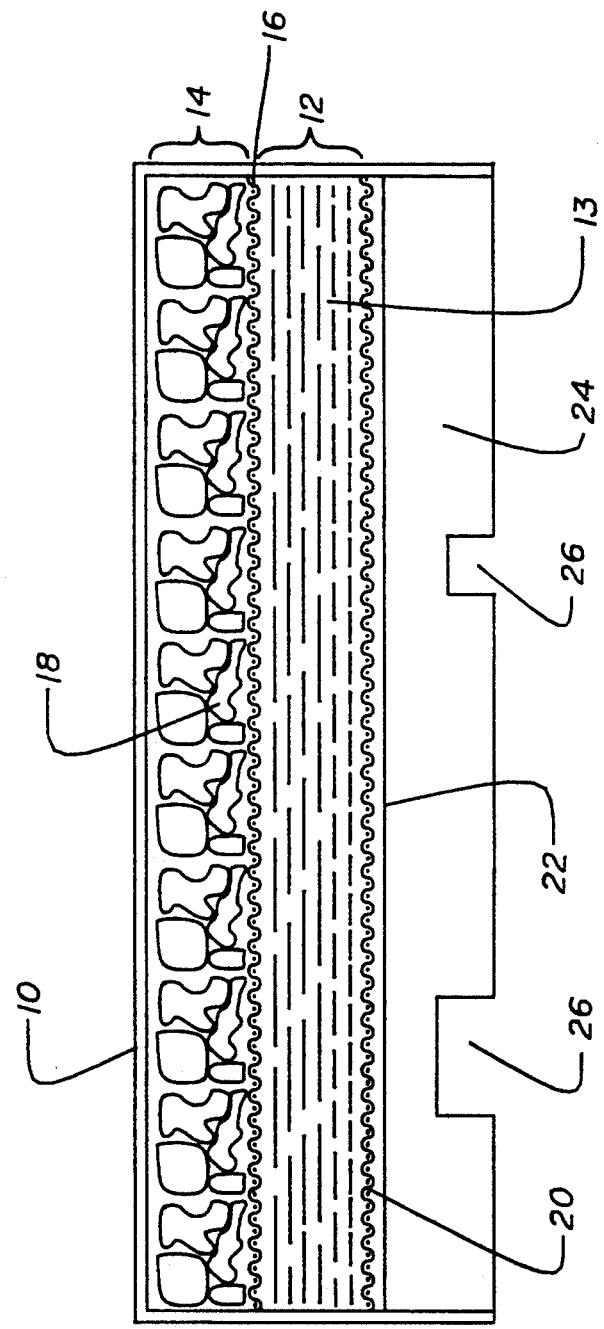

INSECT BAIT STATION

This application is a continuation of application Ser. No. 07/523,011 filed May, 14, 1990 now abandoned.

This application is a continuation of application U.S. Ser. No. 07/523,011, abandoned which is related to co-pending application U.S. Ser. No. 07/389,598, filed Aug. 3, 1989, Pat. No. 5,141,744, the disclosure of which is incorporated by reference herein.

BACKGROUND OF THE INVENTION

1) Field of the Invention

This invention relates to a device for biological control of insects, more particularly to a biological insect bait station wherein insect parasitic nematodes are consumed by insect pests such as cockroaches, ants and termites.

2) Description of Related Art

Various devices are known in the prior art for control of insects. Generally, the prior art bait devices comprise a housing having a top portion and a bottom portion. The bottom portion typically includes means for entry of the insect into the bait device and further typically includes a baiting ingredient or attractant for attracting the insect into the device. After being drawn into the bait device by the attractant, the insect is typically subjected to an insecticide material.

The insecticide utilized in the prior art devices is either an ingestible insecticide or a contact insecticide. In the prior art devices, chemicals of questionable environmental compatibility are generally used.

It is the object of this invention to provide an insect bait station which uses biological insecticides rather than toxic chemicals. A further object is to provide a method for attracting insects to the bait station, and once they are attracted, to stimulate consumption of the biological insecticide. These and other objects of the invention may be obtained without undue contamination of the environment with toxic chemicals. In particular the device of this invention does not expose the user to hazardous chemicals during transport or installation of the device, and further the device of this invention does not present a waste disposal problem in that the components are naturally occurring, biodegradable materials.

SUMMARY OF THE INVENTION

These and other objects of the invention are achieved by the provision of a device for environmentally sensitive management of noxious insects in which extermination of the insects is provided by ingestion of natural entomopathogens. The device contains a reservoir of water for the entomopathogens in order to maintain their viability for a time sufficient to effect the desired extermination. The device further comprises attractants and feeding stimulants for the insects.

BRIEF DESCRIPTION OF THE DRAWING

The Figure illustrates a typical insect bait station.

DETAILED DESCRIPTION OF THE INVENTION

The Figure shows a representative biological insect bait station in position for use. The configuration can be round, square, rectangular or otherwise. The bait station comprises a container 10 having two compartments 12 and 14, separated by a physical barrier 16, such as a semipermeable membrane or a screen. Compartment 14 contains fully swelled water-retentive polymer gel or gel pieces 18. Compartment 12 contains biological insecticides such as insect nematodes dispersed in a suitable medium 13. A second screen 20 is placed over compartment 12 to hold the gel in place. A removable cover 22 is provided to prevent evaporation during storage. Protective cover 24 surrounds the entire station and is provided with a plurality of portals 26, which may all be the same size and shape or may be of different sizes and shapes. Optionally, cover 24 and container 10 are one piece.

In one embodiment the insect nematodes initially are suspended in a polysaccharide solution (e.g. a gellan gum) which also contains approximately 25% of swelled and crushed water retentive polymer gel pieces as described above. This suspension is added to a container having a layer of fully swelled water retentive polymer gel, optionally covered with a fine mesh screen. The suspension can be induced to gel by adding cations, preferably divalent cations such as calcium or magnesium ions. Once gelled, the insect nematodes are immobilized in a soft, moistening environment which greatly enhances their survival during subsequent usage. The top of the nematode gel is then covered with a soft, fine mesh screen; this screen is, in turn, covered with a removable or peelable water repellent paper or soft plastic to prevent evaporation during storage. Before use, the device is put into a tight, dark protective cover made of either plastic or hard paper. The height of this protective cover is about 1½ times that of the bait station containing insect nematodes. Portions of this protective cover are cut out to provide multiple entrance points for insects when placed upside-down. Immediately before use, the peelable material on top of the soft screen of the upper compartment is removed and the device is placed upside down in an area infested with insects.

The bait stations may be custom designed to suit the particular insects whose control is desired. For example, a cockroach bait station may have a ¼ inch to ⅜ inch layer of water retentive polymer gel and ¼ inch to ⅜ inch layer of pathogen dispersion and a ¼ inch to ½ inch open area at the bottom. The portals for cockroaches then would be 3/16 inch to ¼ inch high to provide tactile stimulation to the entering roaches. A suitable attractant for cockroaches would be included in or in effective proximity to the bait station. In the station custom designed for ants and termites the portals would have a height of about 1/16 to about ⅛ of an inch and the pathogen gel would be about ⅛ to about ¼ inch thick. Suitable ant and termite attractants would be similarly provided.

By putting the insect bait station upside-down in a dark protective cover, the insect nematodes will stay moist for an extended period to up to 2 months. The presence of water retentive polymer in the bait station will constantly supply water to the nematodes. Water is reported to be an excellent attractant for cockroaches. Cockroaches can further be attracted to the bait station by specific pheromones. In one application, the pre-made pheromones can be stuck to the side of cover near the cockroach entrance. Alternatively, one can simply strike the side of cover with a pheromone "stick". Once cockroaches are attracted to the "bait station", the presence of water will then induce them to drink the solution containing insect nematodes. Certain sugar derivatives such as raffinose can act as a feeding stimulant.

The active ingredient in the insect bait station of this invention comprises the entomopathogens distributed within a gelled matrix. The problem of desiccation of the entomopathogens is substantially ameliorated by their macroencapsulation in the gel. Since the entomopathogens are distributed in a continuous insect consumable matrix, along with a source of water for the entomopathogens, their ·viability is significantly enhanced. The final product is a continuous gel in which the nematodes or the like are embedded, together with a source of moisture, and, optionally, other additives, such as insect attractants, insect feeding stimulants, and such stabilizers as may be required by the contemplated use of the insect bait device.

By one process used in this invention, the entomopathogens are suspended in an aqueous solution of a gel-forming matrix in the presence of an inert water retaining polymer. Gelation is then induced by whatever means are appropriate for the selected matrix. The resultant insecticidal macrogel then contains a distribution of entomopathogens and water reservoirs. The macrogel may be stored for an indefinite period without adverse effects on the viability of the entomopathogens and may be cut into smaller pieces as desired.

The gel-forming matrix is selected from natural, naturally derived, and synthetic polymers, with the provisos that the matrix per se and the gelation conditions are neither harmful to the entomopathogens nor interfere with the effectiveness of the pathogens. Suitable gel-forming matrices include, but are not limited to, agarose, carbopols, carrageenan, dextran, guar gum, and other heteropolysaccharides, such as gellan gum. One advantage associated with the use of the natural polysaccharides is that these are often attractive as food for the insects whose demise is desired. A preferred matrix is the cationically gellable heteropolysaccharides, such as those disclosed in U.S. Pat. No. 4,326,052 and U.S. Pat. No. 4,326,053, the disclosures of which are incorporated by reference herein. A suitable variety of this material is available commercially as Gel-Gro (R) gellan gum from ICN Biochemicals, Cleveland, Ohio.

An important aspect of the hydromacroencapsulation process is the selection of a gel-forming material which is a liquid at room temperature or at temperatures which are not detrimental to the entomopathogens and which can be induced to gel at a predetermined time by either mixing or spraying with a gelling agent. Such controlled gelation is important during manufacturing of the gels to avoid premature gelation and clogging of equipment. During the production of macrogels in discrete containers, a gelling time of 2 to 15 minutes is preferred.

The gelation time of the Gel-Gro (R) gellan gum used in the Examples which follow is easily controlled by varying the polymer concentration, the concentration and type of gelling agent, and the temperature. Preferably, the Gel-Gro liquid polymer concentration is between 0.2% and 5.0% by weight, the gelling agent is a cation, and the concentration of gelling agent is from 0.1 mM to 500 mM. Most preferably, the polymer concentration is from about 0.6% to 1.2% by weight, the gelling agent is a divalent cation, and the cation concentration is from about 0.5 mM to 25.0 mM. The most preferable conditions result in gelation times of about 1 to 15 minutes. When spraying formulations are desired, a cation concentration in excess of 25 mM is preferred to obtain rapid gelation.

Suitable divalent cations include barium, calcium, copper(II), iron(II), magnesium, manganese, and zinc(II). Monovalent cations such as ammonium, cesium, lithium, potassium, and sodium, may also be used to induce gelation, albeit at higher concentrations. Trivalent ions such as aluminum and iron(III) are also useful.

The hydrated, water retentive compound which is incorporated into the gel as the water reservoir for the entomopathogen is typically a water-absorbing polymer, such as a hydrophilic acrylic, acrylamide, polyurethane or starch-based polymer. Such polymers, commonly known as hydrogels, will absorb and retain several hundred times their weight in water and will slowly release the absorbed water. Representative examples of these materials are California Crystals (R), a water-absorbing acrylic polymer available from J & G Agrow-tek, Rancho Cordova, Calif. and Water Grabber(R), a water-absorbing acrylamide from FP Products, Inc., Atlanta, Ga. Other materials which exhibit similar affinities for water may be substituted. The amount of hydrated, water retentive polymer present in the matrix is generally about 25% to about 75%, although the choice and concentration of pathogen and the envisioned environment may lead to significant departures from these norms. Optionally, a heteropolysaccharide, such as Gel-Gro (R) gellan gum, may be used without water retentive polymer, if the intended use permits of this approach.

As previously noted, the entomopathogen is selected from among those pathogens which control noxious insect infestations. Baculoviruses, such as nuclear polyhedrosis virus, bacteria, such as *Bacillus thuringiensis*, fungal pathogens, such as *Beauveria bassiana, Metarrhizium anisopliae,* and *Nomuraea rileyi*, and nematodes, such as *Neoaplectana carpocapsae*, (also known as *Steinernema feltiae* and *Steinernema carpocapsae*) and *Heterorhabditis heliothidis* are among the more useful pathogens. Selection of the entomopathogens is not limited to those described herein, but is well within the purview of one skilled in the art of natural predation. Nematodes are particularly well-suited for the practice of this invention. However, the only limitations on the pathogens are that they not be inactivated by the conditions of gelation or the composition of the macrogel. Since the entomopathogens will reproduce in the insect host, only a few need be incorporated in a discrete sample of gel to provide control. Of course, millions of pathogens may be easily incorporated. In the practice of this invention, we have found that nematode concentrations of up to about 500,000 per milliliter are most useful. For other pathogens, such as *Bacillus thuringiensis*, the gel may contain as much as 20% by weight.

A further aspect of the current invention is the optional use of agents capable of attracting insects to the bait station and stimulating the insects to feed on the gels. Such agents, also termed baits, can include, for example, foods used in the commercial rearing of insects, pheromones, chemical attractants, and the like. Art-recognized insect attractants include sucrose, wheat germ, and bran. In the course of this development, it has been discovered that raffinose is a highly effective feeding stimulant for certain insects.

The following examples are presented to illustrate the basic features of the invention but are not intended to, and should not be construed as, placing any undue limitations on the invention as claimed.

EXAMPLE 1

A solution of purified gellan gum (Gel-Gro (R) gellan gum) was prepared by dissolving 0.2 g of the gum in 10 mL of hot deionized, distilled water to make a 2% solution. This solution was cooled and held at 35° to 37° C.

A stock of fully swelled and expanded water retentive polymer was prepared by soaking small crystals of a water-swellable acrylic polymer (California Crystals) (R) in water for about one day. The swollen crystal gels were then pushed through a wire screen to produce pieces that were approximately 1 mm in length, width, and height. Enough water swollen pieces were added to a 1 mL aqueous dispersion containing approximately 10,000 nematodes (*Neoaplectana carpocapsae*) to increase the volume to 2 mL.

To this nematode dispersion, 2 mL of the 2 wt % gellan gum solution was added with gentle mixing. 0.2 mL of 20 mM calcium chloride was then added and the resultant mixture quickly poured into plastic tubes. Gelation was complete in about ten minutes and the tubes were then capped.

When capped, the insecticidal nematode macrogels are stable for at least one year when stored at 16° C. or lower. At room temperature, the macrogels retain biological activity for at least six months.

When nematode-containing macrogels without water retentive polymers were uncapped and exposed at room temperature, the macrogels dehydrated rapidly, and after one week, the gels were totally dry and few live nematodes were present. In contrast, uncapped nematode-containing macrogels with water retentive polymer were still moist after one week at room temperature and at least 95% of the nematodes were still alive.

EXAMPLE 2

A 2% gellan gum solution was prepared as in Example 1. To this solution was added with vortexing an equal volume of the nematode-water retentive polymer dispersion of Example 1, also containing 2 mM calcium chloride. The resulting macrogel was then capped and stored below 16° C.

EXAMPLE 3

A nematode-containing macrogel was prepared following the procedure of Example 2 in plastic test tube caps (1 cm diameter, 1.8 cm height). Raffinose (2% by weight) was also present in the nematode-water retentive polymer dispersion. Two of these macrogel samples were placed in a large tray (40×20 cm, 15 cm high), layered with wood shavings and having both water and gourmet insect diet present. Ten German cockroaches (*Blatella germanica*) were introduced into the tray. After 3 days, all the cockroaches were dead. When dissected 4 days later, each contained 10 or more live nematodes within the body. Nematode-free macrogel placed in a control tray had no effect on cockroaches.

EXAMPLE 4

Nematode-containing macrogels prepared as in Example 3 were tested for efficacy against a representative cross-section of insect pests. The tests were conducted in 250 mL beakers containing both insect food and a source of water. The results are summarized below.

| INSECT | TIME TO KILL | NEMATODES IN BODY CAVITY 10 DAYS LATER |
|---|---|---|
| Southern armyworm (*Spodoptera eridania*) | <2 days | 1000 |
| Mexican Bean Beetle (*Epilachna varivestis*) | <2 days | 500 |
| Black cutworm (*Agrotis ipsilon*) | 1-2 days | 1000 |
| Boll weevil (*Anthonomus grandis*) | <2 days | Not Counted |
| Tobacco budworm (*Heliothis virescens*) | <3 days | Not Counted |
| Corn rootworm (*Diabrotica spp.*) | 1-2 days | 250 |
| Tobacco hornworm (*Manduca sexta*) | 1-2 days | 10,000 |

EXAMPLE 5

A 2.0% agarose solution was prepared by dissolving 0.2 g of agarose in 10 mL of distilled water in a boiling water bath for approximately 5 minutes. The solution was cooled to 60° C. and maintained at this temperature in a constant temperature water bath to prevent premature gelation. A stock of fully swelled and expended water retentive polymer was prepared by soaking small crystals of water-swellable acrylic polymer in water for 1 day. The swollen crystal gels were then pushed through a wire screen to produce pieces that were approximately 1 mm in length, width, and height. Enough water swollen pieces were added to 1 ml aqueous dispersion containing approximately 10,000 nematodes (*Neoaplectana caprocapsae*) to increase the volume to 2 mL.

Two ml of agarose solution in a test tube previously maintained at 60° C. were taken out of the water bath and cooled to about 45° C. To this agarose solution, 2 mL of the above nematode-water retentive polymer dispersion were added with vortexing and the resulting mixture was poured immediately into a mold. Gelation occurred in about 5 to 10 seconds. The nematode macrogels in agarose were then covered with parafilm. The insect nematode agarose macrogels were stable for at least one year when stored below 16° C. Similar insect nematode macrogels have been prepared using carrageenan, agar, kappa-carrageenan, carbopol and guar gum, all with retention of activity.

EXAMPLE 6

A 2% gellan gum solution was prepared as described in Example 1. Enough water swollen pieces of water retentive polymers were added to a 1 mL aqueous suspension containing 4 mM calcium chloride and nuclear polyhedrosis viruses (NPV) isolated from diseased wax moth larvae to make a 2 mL solution (final concentration of calcium chloride was 2 mM). This NPV-water retentive polymer solution was then added with gentle vortexing to an equal volume of the 2% gellan gum solution and quickly poured into plastic tubes. Gelation took approximately 10 minutes and the NPV macrogel tubes were then capped and stored at below 16° C. The NPV macrogels were stable for at least six months.

EXAMPLE 7

A 2% gellan gum solution was prepared as described in Example 1. Enough water swollen pieces of water retentive polymers were added to a 1 mL solution of crystal-spore complexes (2.5 mg/mL) from *Bacillus thuringiensis* subsp. kurstaki (Bt) containing 4 mM calcium chloride to make a 2 mL solution. To this solution was added, with gentle vortexing, 2 mL of the 2% gellan gum solution and the resultant mixture was poured into plastic tubes. Macrogel tubes were then capped and stored below 16° C. The Bt crystal-spore macrogels were stable for at least six months.

Macrogels containing both Bt crystal-spore complexes and approximately 10,000 nematodes (*Neoaplectana carpocapsae*) were also prepared as described above by mixing these two entomopathogens together with gellan gum. Various macrogels were then cut into small cubes of 0.5 cm in length, width and height and placed on top of a diet for tobacco hornworms (*Manduca sexta*) in plastic containers measuring 3 cm in diameter and 10 cm in height. The combined insect nematode-Bt crystal macrogels were found to be more active against tobacco hornworms than either nematode macrogels or Bt crystal macrogels alone. Control macrogels without entomopathogens were inactive against tobacco hornworms.

EXAMPLE 8

A 2% gellan gum solution was prepared as described in Example 1. Enough water swollen pieces of water retentive polymers were added to a 1 mL aqueous suspension of fungal pathogen (*Beauveria bassiana*) spores containing small amounts of Tween-20 and 4 mM calcium chloride to make a 2 mL solution. The fungal pathogen-water retentive polymer dispersion was then added, with gentle vortexing, to 2 mL of gellan gum solution. The resultant mixture was poured into plastic tubes, capped, and stored below 16° C. These macrogels were stable for at least several months. Similar macrogels were also prepared from fungal pathogens *Metarrhizium anisopliae* and *Nomuraea rileyi*, all with retention of activity.

EXAMPLE 9

A 2% gellan gum solution was prepared as described in Example 1. Enough water swollen pieces of water retentive polymers were added to a 1 mL solution of crystal-spore complexes (2.5 mg/mL) from *Bacillus thuringiensis* subsp. kurstaki (Bt) containing 4 mM calcium chloride and 10% UV protectant Octyl-dimethyl PABA to make a 2 mL solution. To this solution was added, with vortexing, 2 mL of the 2% gellan gum solution. The resultant mixture was poured into plastic tubes, capped and stored below 16° C. The Bt crystal macrogels containing UV protectant were stable for at least six months. The hydrophobic nature of the UV protectant allows them to concentrate on top of the macrogels which offer advantage for protection against inactivation by sunlight. When the UV protectant-containing Bt macrogels were challenged with UV by irradiation with a GE germicidal lamp at a distance of 10 cm for 1 hour, full retention of biological activity against tobacco hornworms (*Manduca sexta*) was observed. Dimunition of activity was observed for unprotected macrogels.

EXAMPLE 10

This example illustrates the utility of an insect bait station of this invention for controlling infestation of cockroaches.

A nematode gel was prepared from a solution of 1.2% Gel-Gro polymer, containing 25% crushed water retentive polymer (California Crystals). Following the introduction of approximately 2000 nematodes, gelation was induced with 5 mM calcium chloride.

Swelled water retentive polymer gel pieces were introduced into the bottom of a Petri dish. The water retentive polymer layer was covered with a hard nylon screen. A layer of the insecticidal macrogel was then placed on top of the screen. A second screen was applied on top of the nematode gel. The bottom and sides of the dish were then covered with a semi-rigid black construction paper which extended slightly above the upper surface. Several cuts were made in the protruding section of the construction paper to act as entrances into the insect bait device. The device was then inverted and placed on the floor so that the gel layer was a few millimeters above the floor surface. The table below reports the effect of the bait station upon an infestation of cockroaches. The number of dead roaches versus total roaches over a period of six days is given.

In addition to the gel described above, a gel containing 1% raffinose as an attractant was also prepared and evinced more rapid mortality versus the raffinose-free gel.

| | Number of Days | | | | | | |
|---|---|---|---|---|---|---|---|
| | 0 | 1 | 2 | 3 | 4 | 5 | 6 |
| Control (plain gel) | 0/10 | 0/10 | 0/10 | 0/10 | 1/10 | 1/10 | 1/10 |
| Nematode gel | 0/10 | 1/10 | 1/10 | 1/10 | 6/10 | 6/10 | 7/10 |
| Nematode gel +1% raffinose | 0/9 | 0/9 | 4/9 | 5/9 | 7/9 | 8/9 | 9/9 |

EXAMPLE 11

Household pests such as German cockroaches can be controlled using other nematode bait station formulations. Approximately 2,000 nematodes were dispersed in 2.5 mL of water containing 2% raffinose and mixed with 5.0 mL of Crisco (R) shortening and 2.5 mL of crushed swelled water retentive polymer gel pieces. An additional 5 to 10 mL of large swelled water retentive polymer pieces were also dispersed in the mixture. The resultant nematode formulation was transferred to a 35×15 mm tissue culture dish and covered with a soft nylon screen. This resulting nematode dish is then put into a dark plastic or construction paper container with approximately 10 mm extra height and sections of it cut off. This device is then placed upside-down with the cut-out sections of container providing multiple entrance points for cockroaches. The above cockroach bait station was placed in a 30×12 inch tank containing 10 German cockroaches (*Blatella germenica*), wood shavings, dog chow (Purina) as a competitive food source, and a water dish.

All cockroaches were dead in seven days. Furthermore, adult females were killed with egg cases still attached and became totally dry. Thus, unlike current chemical roachicides, the adult female cockroaches did not perceive to be poisoned when they ingested nematodes. Very few, if any, nymph cockroaches that were present were due to those hatched from eggs before the females ingested the nematodes. Control bait station without nematodes did not show any cockroach mortality.

What is claimed is:

1. A device for environmentally sensitive management of noxious insects, comprising in cooperative combination, a first compartment and a second compartment, said first compartment having entomopathogens dispersed in a continuous insect-consumable matrix which does not inactivate said entomopathogens, said second compartment containing a reservoir of water in liquid form for the entomopathogens, said device having two configurations: an upright configuration and an inverted configuration, said first and second compartments separated by a barrier adapted to permit the transfer of water from said second compartment to said first compartment by gravity in said inverted configuration, wherein said first compartment and said second compartment are vertically disposed with respect to one another, said device having a plurality of portals for ingress and egress of the insects.

2. A device of claim 1 in which the insect-consumable matrix is selected from the group consisting of natural and synthetic polymers.

3. A device of claim 2 in which the insect-consumable matrix is selected from the group consisting of agarose, dextran, carrageenan, gellan gum, and guar gum.

4. A device of claim 2 in which the insect-consumable matrix is a polymerized carbopol.

5. A device of claim 2 in which the insect-consumable matrix is a kappa-carrageenan.

6. A device of claim 2 in which the insect-consumable matrix is a heteropolysaccharide.

7. A device of claim 6 in which the heteropolysaccharide is a cation-induced gel of an anionic gellan gum.

8. A device of claim 1 further comprising a water retentive compound dispersed in the insect-consumable matrix of said first compartment.

9. A device of claim 8 in which the water retentive compound is a hydrophilic acrylic, acrylamide, vinyl, polyurethane or starch-based polymer.

10. A device of claim 1, having a water retentive compound in said second compartment.

11. A device of claim 1 in which the entomopathogens are selected from the group consisting of nematodes, bacteria, baculoviruses, and fungal pathogens.

12. A device of claim 11 in which at least one entomopathogen is an insect nematode selected from the group consisting of *Neoaplectana carpocapsae* and *Heterorhabditis heiothidis*.

13. A device of claim 11 in which the entomopathogens are nuclear polyhedrosis viruses.

14. A device of claim 11 in which the entomopathogens are *Bacillus thuringiensis* or the crystal spore complexes thereof.

15. A device of claim 11 in which the entomopathogens are selected from the group consisting of *Beauveria bassiana, Metarrhizium anisopliae,* and *Nomuraea rileyi.*

16. A device of claim 1 further comprising at least one agent capable of attracting insects to the device, said agent included in, coated on, or in effective proximity to, said device.

17. A device of claim 1 further comprising at least one agent for stimulating ingestion of the macrogel by the target insect.

18. A device of claim 17 in which said agent is a saccharide selected from the group consisting of glucose, sucrose, mannose, and raffinose.

19. A device of claim 1 comprising as said compartment an insecticidal macrogel having at least one species of insecticidal nematode, a hydrated water retentive compound to provide sufficient water to maintain the viability and infectivity of said nematodes and to maintain the softness and ease of consumption of the macorgel, all dispersed in a layer of gelled polysaccharide; said second compartment consisting essentially of a hydrated water retentive compound; means for permitting liquid water transport from the second compartment to the first compartment; means for entry of insects; and an outer container.

20. A device of claim 19 further comprising a quantity of at least one compound for attracting insects to or stimulating ingestion of the macrogel by insects.

21. A device of claim 19 in which the means for entry are adapted to provide tactile stimulation to cockroaches.

22. A device of claim 19 in which the means for entry are adapted to receive ants and termites.

* * * * *